(12) United States Patent
Gunther et al.

(10) Patent No.: US 9,852,507 B2
(45) Date of Patent: Dec. 26, 2017

(54) REMOTE HEART RATE ESTIMATION

(71) Applicants: Jacob Gunther, North Logan, UT (US); Nathan E. Ruben, Logan, UT (US)

(72) Inventors: Jacob Gunther, North Logan, UT (US); Nathan E. Ruben, Logan, UT (US)

(73) Assignee: Utah State University, Logan, UT (US)

( * ) Notice: Subject to any disclaimer, the term of this patent is extended or adjusted under 35 U.S.C. 154(b) by 48 days.

(21) Appl. No.: 14/937,506

(22) Filed: Nov. 10, 2015

(65) Prior Publication Data

US 2016/0132732 A1 May 12, 2016

Related U.S. Application Data

(60) Provisional application No. 62/077,766, filed on Nov. 10, 2014.

(51) Int. Cl.
*G06K 9/00* (2006.01)
*G06T 7/00* (2017.01)
(Continued)

(52) U.S. Cl.
CPC ........ *G06T 7/0081* (2013.01); *A61B 5/02416* (2013.01); *G06K 9/00342* (2013.01);
(Continued)

(58) Field of Classification Search
CPC ........................... G06T 7/0081; G06K 9/00342
See application file for complete search history.

(56) References Cited

U.S. PATENT DOCUMENTS

2007/0085690 A1 4/2007 Tran
2007/0208266 A1 9/2007 Hadley
(Continued)

FOREIGN PATENT DOCUMENTS

EP 2438849 A1 4/2012
EP 2767233 A1 8/2014
EP 2774533 A1 9/2014

OTHER PUBLICATIONS

Ruben, Nathan E., Remote Heart Rate Estimation Using Consumer-Grade Cameras, All Graduate Plan B and other Reports, Paper 463, Jan. 1, 2015, Utah State University, Logan, Utah.
(Continued)

*Primary Examiner* — Oneal R Mistry

(57) ABSTRACT

For remote heart rate estimation, a method detects an object of interest (OOI) in each image of a video data and tracks the OOI in each image of the video data. The method identifies a region of interest (ROI) within the OOI and generates a plurality of super pixels from a plurality of pixels in each ROI. The method further generates a super-pixel time series from the plurality of super pixels in each image and removes interfering signals from the super-pixel time series. The method further models the super-pixel time series as a super-pixel model and calculates a heart beat signal from the super-pixel model. The method calculates heart characteristics from the heart beat signal. The heart characteristics include one or more of a heart rate, an inter-beat interval, and a heart rate variability.

20 Claims, 10 Drawing Sheets

(51) Int. Cl.
*A61B 5/024* (2006.01)
*G06T 7/246* (2017.01)

(52) U.S. Cl.
CPC .... *G06T 7/248* (2017.01); *G06K 2009/00939* (2013.01); *G06T 2207/10024* (2013.01); *G06T 2207/10048* (2013.01); *G06T 2207/30048* (2013.01); *G06T 2207/30088* (2013.01)

(56) References Cited

U.S. PATENT DOCUMENTS

| 2011/0251493 | A1 | 10/2011 | Poh et al. | |
|---|---|---|---|---|
| 2014/0161421 | A1* | 6/2014 | Shoemaker | G11B 27/028 386/278 |
| 2015/0262358 | A1* | 9/2015 | Schormans | G06T 7/0016 382/103 |
| 2016/0089041 | A1* | 3/2016 | Keat | A61B 5/72 600/479 |
| 2016/0196666 | A1* | 7/2016 | Venkatraghavan | G06T 7/254 382/130 |

OTHER PUBLICATIONS

Villanueva, et al., The Use of Physiological Tools to Identify Changes in Affective Responses for Graduate Student-Recently Admitted into a Scientific Discipline, IEEE Frontiers in Education Conference Proceedings, Oct. 22, 2014, pp. 1-5, IEEE, Madrid, Spain.

Poh, et al., Non-contact, automated cardiac pulse measurements using video imaging and blind source separation, May 2010, Optics Express 18 (2010): 10762, Optical Society of America.

* cited by examiner

REMOTE HEART RATE ESTIMATION

CROSS-REFERENCE TO RELATED APPLICATIONS

This application claims priority to U.S. Provisional Patent Application No. 62/077,766 entitled "REMOTE HEART RATE ESTIMATION" and filed on Nov. 10, 2014 for Jacob H. Gunther, which is incorporated by reference.

BACKGROUND

Field

The subject matter disclosed herein relates to heart rate estimation and more particularly relates to remote heart rate estimation.

Description of the Related Art

A subject's heart rate is a useful health and fitness metric.

BRIEF SUMMARY

For remote heart rate estimation, a method detects, by use of a processor, an object of interest (OOI) in each image of a video data and tracks the OOI in each image of the video data. The method identifies a region of interest (ROI) within the OOI and generates a plurality of super pixels from a plurality of pixels in each ROI. The method further generates a super-pixel time series from the plurality of super pixels in each image and removes interfering signals from the super-pixel time series. The method further models the super-pixel time series as a super-pixel model and calculates a heart beat signal from the super-pixel model. The method calculates heart characteristics from the heart beat signal. The heart characteristics include one or more of a heart rate, an inter-beat interval, and a heart rate variability.

BRIEF DESCRIPTION OF THE DRAWINGS

In order that the advantages of the embodiments of the invention will be readily understood, a more particular description of the embodiments briefly described above will be rendered by reference to specific embodiments that are illustrated in the appended drawings. Understanding that these drawings depict only some embodiments and are not therefore to be considered to be limiting of scope, the embodiments will be described and explained with additional specificity and detail through the use of the accompanying drawings, in which.

DETAILED DESCRIPTION OF THE INVENTION

Figure 1A:
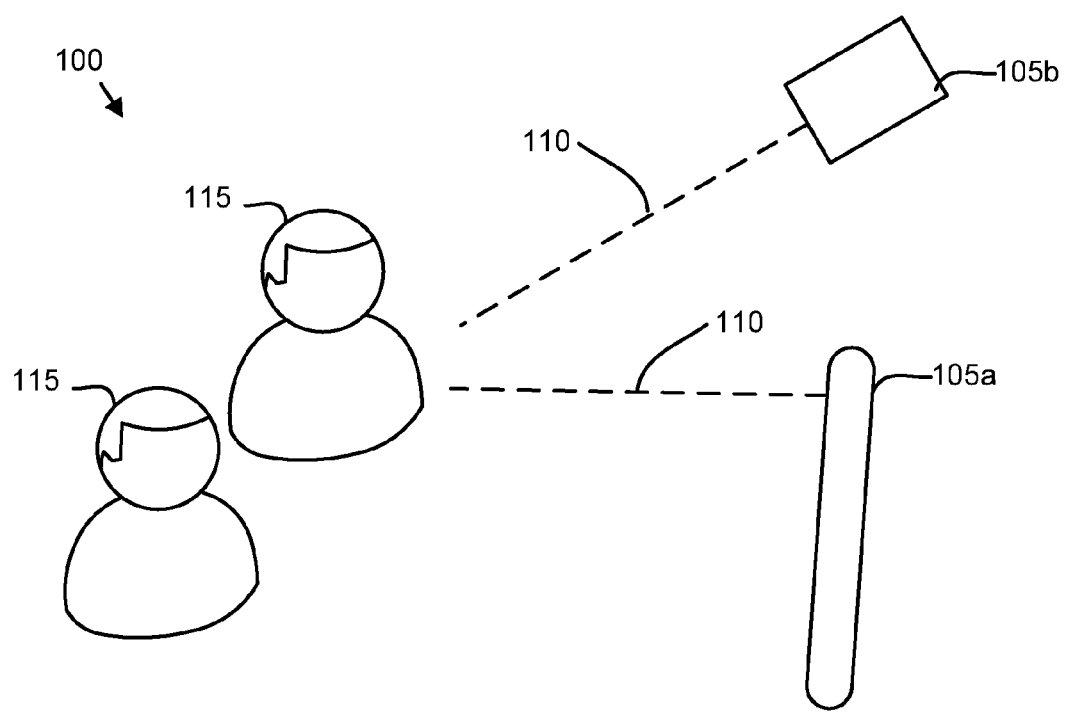
FIG. 1A is a drawing illustrating one embodiment of a heart rate estimation system.

As will be appreciated by one skilled in the art, aspects of the embodiments may be embodied as a system, method or program product. Accordingly, embodiments may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, embodiments may take the form of a program product embodied in one or more computer readable storage devices storing machine readable code, computer readable code, and/or program code, referred hereafter as code. The storage devices may be tangible, non-transitory, and/or non-transmission. The storage devices may not embody signals. In a certain embodiment, the storage devices only employ signals for accessing code.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in code and/or software for execution by various types of processors. An identified module of code may, for instance, comprise one or more physical or logical blocks of executable code which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different computer readable storage devices. Where a module or portions of a module are implemented in software, the software portions are stored on one or more computer readable storage devices.

Any combination of one or more computer readable medium may be utilized. The computer readable medium may be a computer readable storage medium. The computer readable storage medium may be a storage device storing the code. The storage device may be, for example, but not limited to, an electronic, magnetic, optical, electromagnetic, infrared, holographic, micromechanical, or semiconductor system, apparatus, or device, or any suitable combination of the foregoing.

More specific examples (a non-exhaustive list) of the storage device would include the following: an electrical connection having one or more wires, a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Code for carrying out operations for embodiments may be written in any combination of one or more programming languages, including an object oriented programming language such as Python, Ruby, Java, Smalltalk, C++ or the like and conventional procedural programming languages, such as the "C" programming language or similar programming languages. The code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to," unless expressly specified otherwise. An enumerated listing of items does not imply that any or all of the items are mutually exclusive, unless expressly specified otherwise. The terms "a," "an," and "the" also refer to "one or more" unless expressly specified otherwise.

Furthermore, the described features, structures, or characteristics of the embodiments may be combined in any suitable manner. In the following description, numerous specific details are provided, such as examples of programming, software modules, user selections, network transactions, database queries, database structures, hardware modules, hardware circuits, hardware chips, etc., to provide a thorough understanding of embodiments. One skilled in the relevant art will recognize, however, that embodiments may be practiced without one or more of the specific details, or with other methods, components, materials, and so forth. In other instances, well-known structures, materials, or operations are not shown or described in detail to avoid obscuring aspects of an embodiment.

Aspects of the embodiments are described below with reference to schematic flowchart diagrams and/or schematic block diagrams of methods, apparatuses, systems, and program products according to embodiments. It will be understood that each block of the schematic flowchart diagrams and/or schematic block diagrams, and combinations of blocks in the schematic flowchart diagrams and/or schematic block diagrams, can be implemented by code. These code may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the schematic flowchart diagrams and/or schematic block diagrams block or blocks.

The code may also be stored in a storage device that can direct a computer, other programmable data processing apparatus, or other devices to function in a particular manner, such that the instructions stored in the storage device produce an article of manufacture including instructions which implement the function/act specified in the schematic flowchart diagrams and/or schematic block diagrams block or blocks.

The code may also be loaded onto a computer, other programmable data processing apparatus, or other devices to cause a series of operational steps to be performed on the computer, other programmable apparatus or other devices to produce a computer implemented process such that the code which execute on the computer or other programmable apparatus provide processes for implementing the functions/acts specified in the flowchart and/or block diagram block or blocks.

The schematic flowchart diagrams and/or schematic block diagrams in the Figures illustrate the architecture, functionality, and operation of possible implementations of apparatuses, systems, methods and program products according to various embodiments. In this regard, each block in the schematic flowchart diagrams and/or schematic block diagrams may represent a module, segment, or portion of code, which comprises one or more executable instructions of the code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and code.

Jacob H. Gunther and Nate Ruben, "Extracting Heart Rate from Video" and Nathan E. Ruben, "Remote Heart Rate Estimation using Consumer-Grade Cameras" are incorporated herein in their entirety by reference. The description of elements in each figure may refer to elements of proceeding figures. Like numbers refer to like elements in all figures, including alternate embodiments of like elements.

FIG. 1A is a drawing illustrating one embodiment of a heart rate estimation system 100. The system 100 includes one or more electronic device 105 and one or more subject 115. The electronic device 105 may be a mobile telephone, a tablet computer, laptop computer, a computer workstation, a video camera, or the like. The electronic device 105 may capture 110 a video clip of video data of the subject 115 using a camera. In one embodiment, the video data may be captured by one or more of a plurality of cameras, 3-color channel camera, a multispectral n-channel camera, an infra red camera, a depth camera, a 1 pixel sensor, and a servo controlled camera. The 3-color channel camera may be a red/green/blue (RGB) 3-color channel camera. For simplicity, the electronic devices 105 and cameras embodied therein will be referred to hereafter in the singular, although any number of electronic devices 105 and cameras may be employed.

In the past, it has been impractical to calculate a heart rate from a video data of the subject 115 because of motion of the electronic device 105, the motion of the subject 115, and changes in illumination. The embodiments described herein generate a super pixel model from the video data and calculate a heartbeat signal and heart characteristics as will be described hereafter. As a result, the electronic device 105 may accurately estimate the heart rate of the subjects 115.

The subjects 115 may be people or animals. A heart rate may be estimated for the one or more subjects 115 from the video data. The video data may be captured 110 from a face or other body part of the subjects 115. The video data may be captured 110 from one or more of reflected natural light, reflected electrical lighting in the environment, reflected illumination provided by the system by, for example, lasers or infrared light emitting diodes (LEDs), and long-wave thermal infrared emission. In one embodiment, the video data may be of a motion stabilized region of interest (ROI). The ROI may be of the forehead of the subject 115.

Figure 1B:
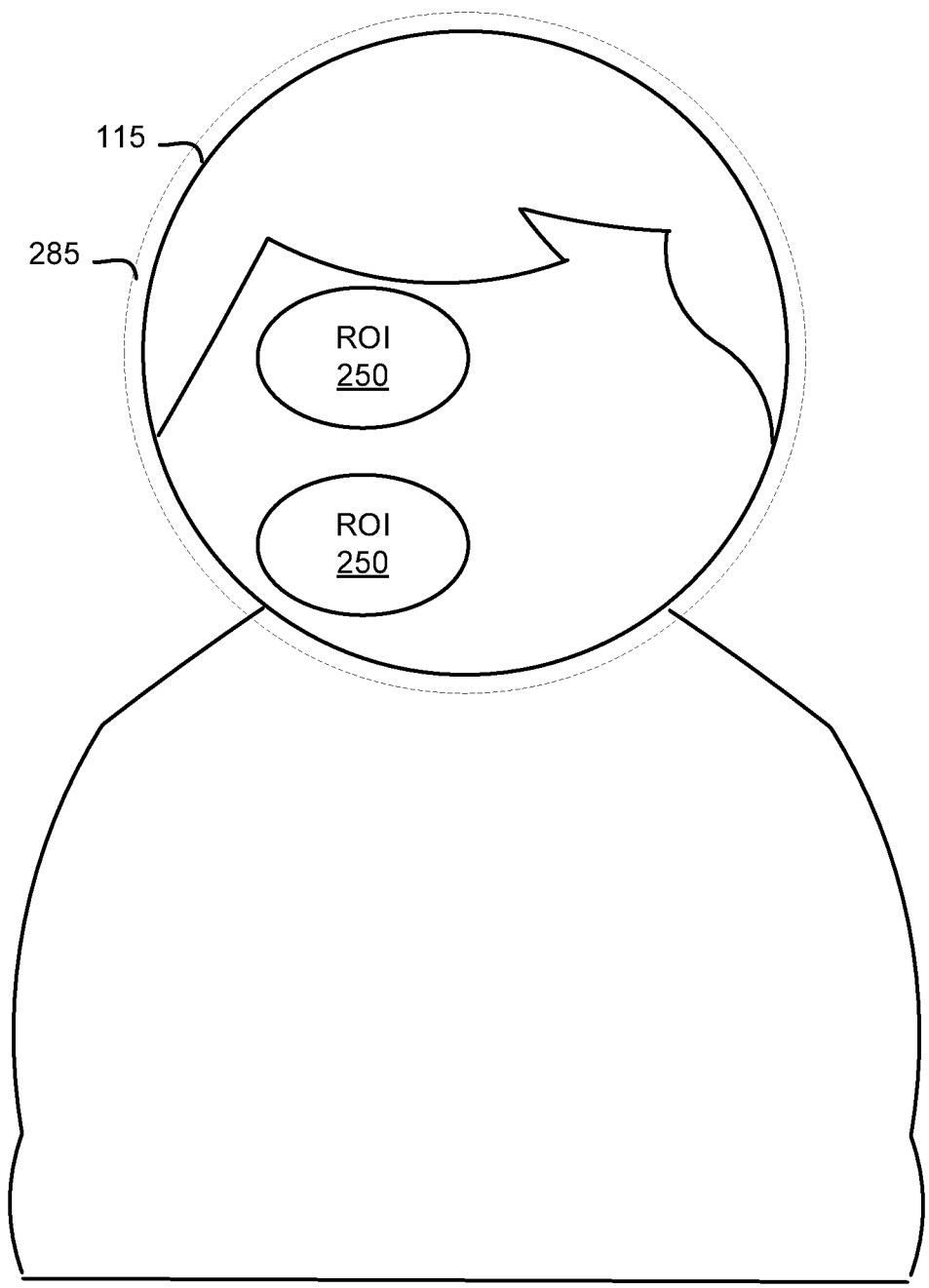
FIG. 1B is a drawing illustrating one embodiment of an OOI and ROI.

FIG. 1B is a drawing illustrating one embodiment of an OOI 285 and ROI 250 on a subject 115. In one embodiment, the electronic device 105 may receive video data and detect the OOI 285 from the video data. The electronic device 105 may detect a face, a portion of the face such as a forehead, a neck, an arm, or other body part as the OOI 285.

The electronic device 105 may further detect and/or track the OOI 285. In one embodiment, the OOI 285 is detected using cascaded object detection on RGB pixels of the video data. The OOI 285 may further be tracked with sub-pixel resolution using spatial correlation-based methods. Alternatively, the OOI 285 may be detected and tracked using infrared band information. For example, a forehead OOI 285 of the subject 115 may be identified from an infrared hotspot. The OOI 285 may also be detected and tracked using multispectral information.

The OOI 285 may be tracked from RGB pixels of the video data using facial landmarks. For example, the electronic device 105 may identify eyes and mouth of a subject 115 from the RGB pixels, and detect the OOI 285 relative to the eyes and mouth. Alternatively, the OOI 285 may be tracked from RGB pixels of the video data using spatial correlation filters.

In one embodiment, the OOI 285 is detected and tracked using information from a depth camera. For example, the depth camera electronic device 105 may identify contours of the subject 115, and a facial OOI 285 may be detected from the contours.

The ROI 250 may be identified within the OOI 285. The ROI 250 may be a specified region within the OOI 285. For example, the ROI 250 may be a forehead or cheek of a head OOI 285. In one embodiment, the OOI 285 and/or ROI 250 are identified from image segmentation. For example, the electronic device 105 may segment the video data into multiple image segments and identify the OOI 285 and/or ROI 250 from the image segments.

The OOI 285 and/or ROI 250 may be detected using a bounding box. The bounding box may include a luma component, blue-difference chroma, red-difference chroma (YCbCr) color space. For example, the OOI 285 and/or ROI 250 may be identified as a region bounded by the YCbCr bounding box. In one embodiment, the electronic device 115 detects and tracks one or more OOI 285 and detects and tracks one or more ROI 250 within each OOI 285.

Figure 1C:
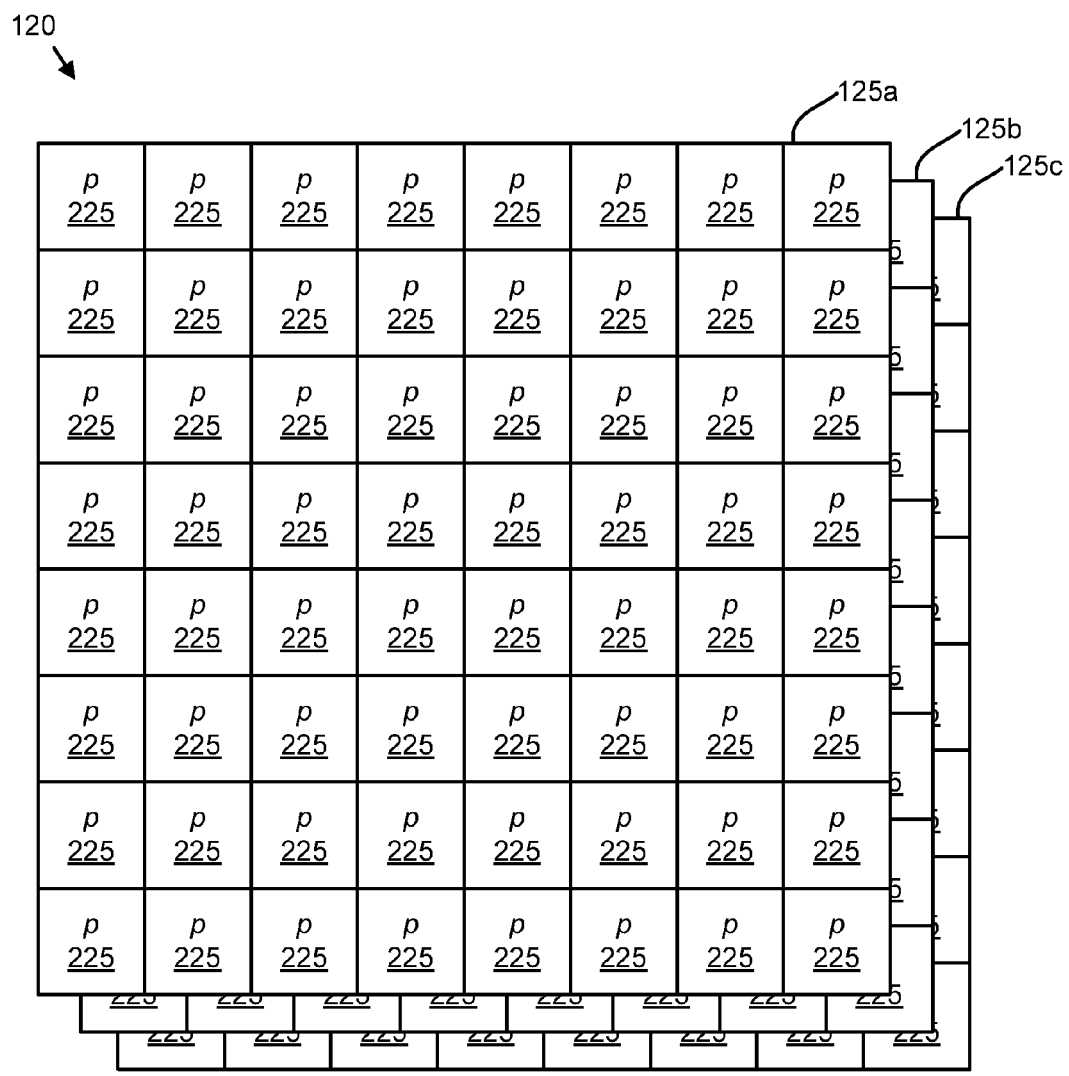
FIG. 1C is a schematic block diagram illustrating one embodiment of video data.

FIG. 1C is a schematic block diagram illustrating one embodiment of video data 120. The video data 120 comprises pixels 225 for a plurality of time series 125. The pixels 225 of a time series 125 may form an image. The video data 120 may organize a data structure in a memory. The time series 125 may be sequential. Alternatively, the time series 125 may be randomly sampled from the video data. The pixels 225 may be RGB, YCbCr, or the like.

Figure 1D:
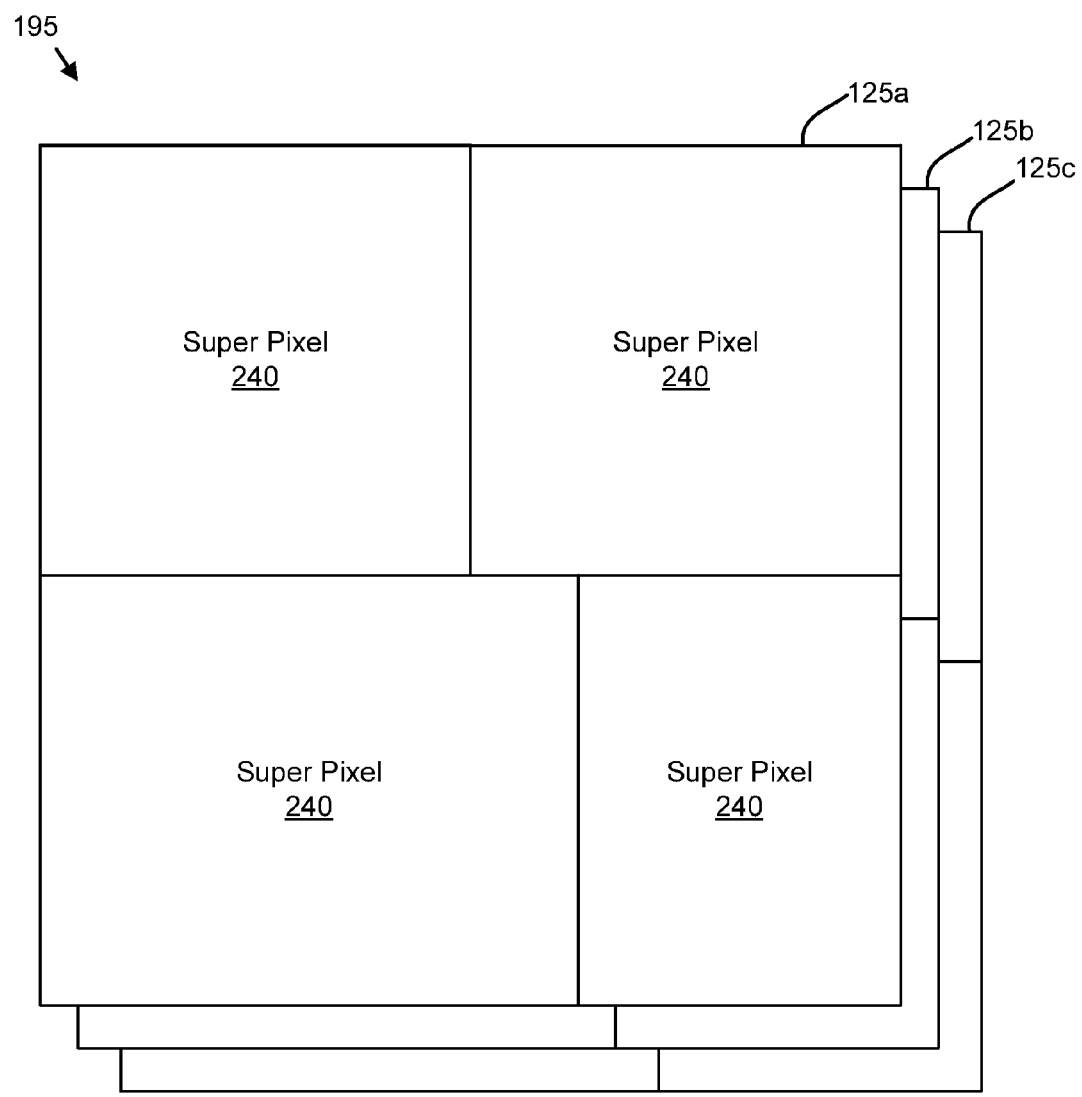
FIG. 1D is a schematic block diagram illustrating one embodiment of a super-pixel time series.

FIG. 1D is a schematic block diagram illustrating one embodiment of a super-pixel time series 195. The super-pixel time series 195 may be organized as a data structure in a memory. In the depicted embodiment, groups of pixels 225 as illustrated in FIG. 1C have been organized into super pixels 240. The generation of the super pixels 240 is described hereafter in FIG. 5. A plurality of time-series 125 may be generated from each super pixel 240 of the video data 120.

Figure 2A:
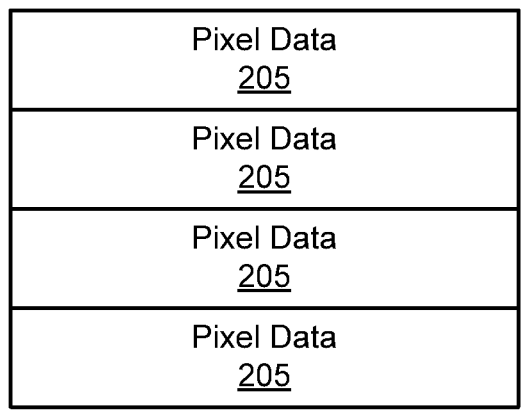
FIG. 2A is a schematic block diagram illustrating one alternate embodiment of video data.

FIG. 2A is a schematic block diagram illustrating one alternate embodiment of video data 120. The video data 120 may be organized as a data structure in a memory. In the depicted embodiment, the video data 120 includes a plurality of pixel data 205. The pixel data 205 may be organized in an array and may store brightness data, contrast data, color data, and the like. In addition, each instance of pixel data 205 may include a pixel identifier. The pixel identifier may be a memory address, matrix indices, and the like.

Figure 2B:
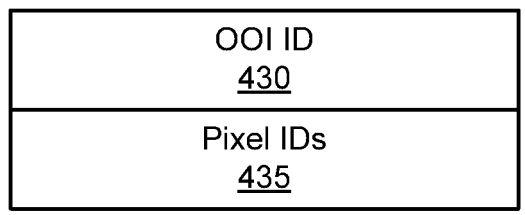
FIG. 2B is a schematic block diagram illustrating one embodiment of OOI data.

FIG. 2B is a schematic block diagram illustrating one embodiment of data 440. The OOI data 440 may be organized as a data structure in a memory. The OOI data 440 may describe an OOI 285. In the depicted embodiment, the OOI data 440 includes an OOI identifier 430 and a plurality of pixel identifiers 435. The OOI identifier 430 may uniquely identify an OOI 285. The pixel identifiers 435 may reference the pixel data 205 for the pixels 225 that comprise the OOI 285.

Figure 2C:
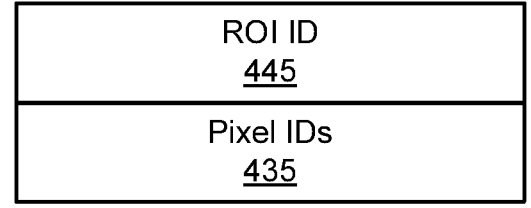
FIG. 2C is a schematic block diagram illustrating one embodiment of ROI data.

FIG. 2C is a schematic block diagram illustrating one embodiment of ROI data 425. The ROI data 425 may be organized as a data structure in a memory. The ROI data 425 may describe an ROI 250. In the depicted embodiment, the ROI data 425 includes an ROI identifier 445 and a plurality of pixel identifiers 435. The ROI identifier 445 may uniquely identify an ROI 250. The pixel identifiers 435 may reference the pixel data 205 for the pixels 225 that comprise the ROI 250

Figure 2D:
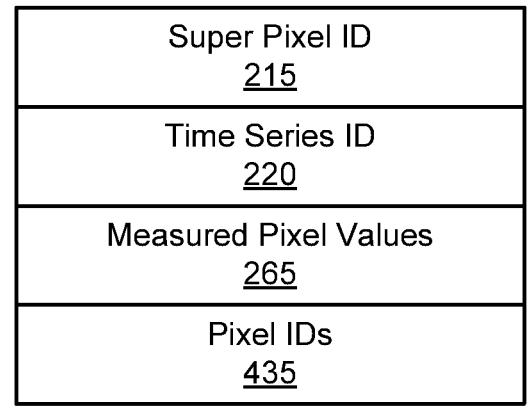
FIG. 2D is a schematic block diagram illustrating one embodiment of super-pixel data.

FIG. 2D is a schematic block diagram illustrating one embodiment of super pixel data 255. The super pixel data 255 may describe a super pixel 240. The super pixel data 255 may be organized as a data structure in a memory. In the depicted embodiment, the super pixel data 255 includes a super pixel identifier 215, a time series identifier 220, measured pixel values 265, and a plurality of pixel identifiers 435.

The super pixel identifier 215 may uniquely identify the super pixel 240. The time series identifier 220 may identify a time series 125 for the super pixel 240. In one embodiment, the time series identifier 220 indicates a position in a sequence. Alternatively, the time series identifier 220 may indicate an absolute and/or relative time. The pixel identifiers 435 may reference the pixel data 205 for the pixels 225 that comprise the super pixel 240.

The measured pixel values 265 may comprise one or more values representing an average value of pixels in the ROI 250. The values may be one or more color values such as RGB values. In addition, the values may include brightness values, contrast values, and the like.

Figure 2E:
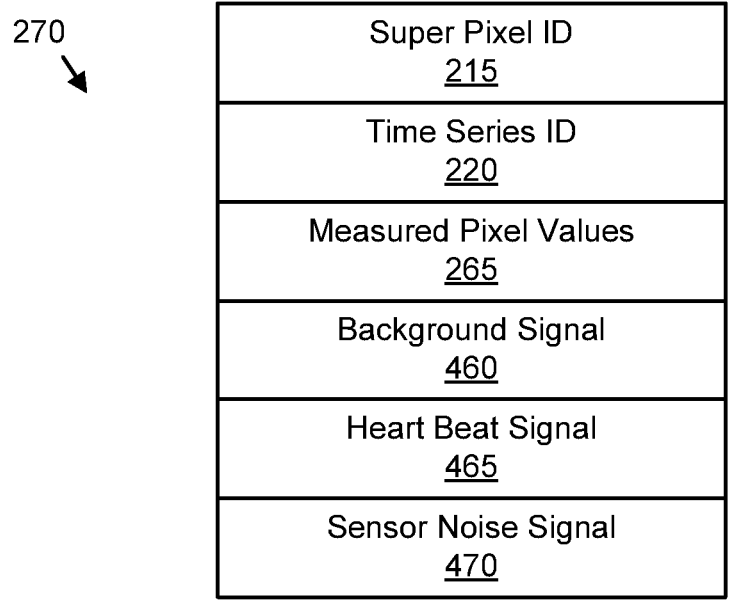
FIG. 2E is a schematic block diagram illustrating one embodiment of a super-pixel model.

FIG. 2E is a schematic block diagram illustrating one embodiment of a super-pixel model 270. The super-pixel model 270 may be organized as a data structure in a memory. In the depicted embodiment, the model 270 includes a super pixel identifier 215, a time series identifier 220, measured pixel values 265, a background signal 460, a heartbeat signal 465, and a sensor noise signal 470.

The super pixel identifier 215 may identify one or more super pixels 240 that are represented by the model 270. The time series identifier 220 may identify one or more time series t 125 represented by the model 270. For example, the time series identifier 220 may identify 48 time series 125 captured during a two second video clip. The measured pixel values $y_i(t)$ 265 may include pixel values for each pixel 225 i in each time series t 125. The background signal $u_i(t)$ 460 may estimate a contribution to the measured pixel values 265 due to movement and lighting variations captured by the electronic device 105 for each pixel 225 i in each time series t 125.

The heart beat signal $h_i(t)$ 465 may estimate a contribution to the measured pixel values 265 due to a heart beat for each pixel 225 i in each time series t 125. The sensor noise signal $n_i(t)$ 470 may estimate contributions to the measured pixel value 265 due to sensor noise in the electronic device 105 for each pixel i 225 in each time series t 125. Thus the super-pixel model 270 for a time series t 125 may be modeled using Equation 1.

$$y_i(t) = u_i(t) + h_i(t) + n_i(t) \quad \text{Equation 1}$$

In one embodiment, the sensor noise signal 470 is assumed to be independent, identically distributed Gaussian noise. In addition, the background signal 460 may be assumed to be smooth. For example, the change in the background signal 460 between time series 125 may be assumed to be less than a background threshold. In one embodiment, the background signal 460 is modeled as a first-order Markov random process. The background signal 460 may be modeled using an auto aggressive model of the first order Markov random process. In one embodiment, the heartbeat signal 465 is assumed to be the same in each super pixel 240. For example, $h_i(t) = h(t)$ may be assumed to be true for all i.

Figure 3:
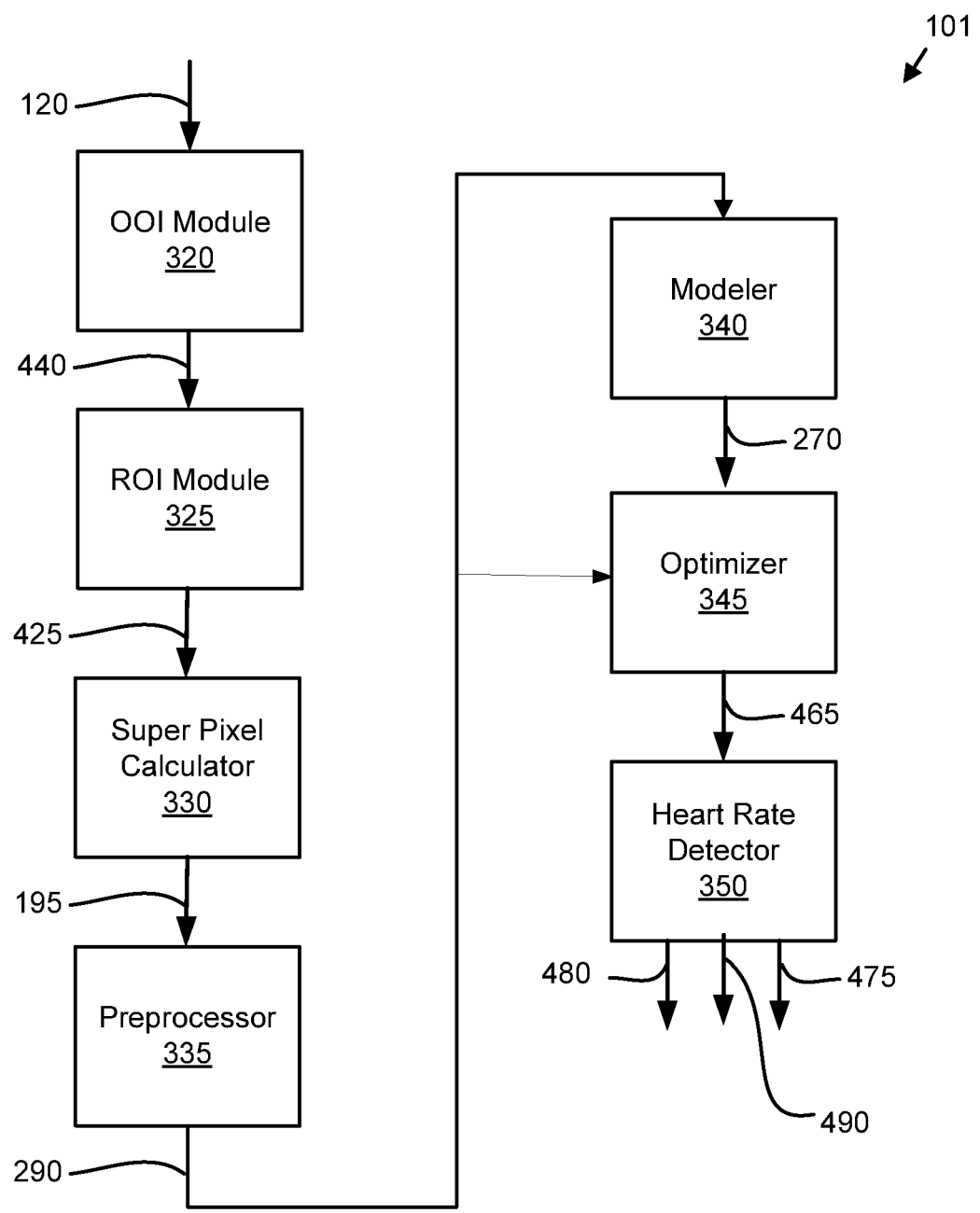
FIG. 3 is a schematic process diagram illustrating one embodiment of a heart rate estimation process.

FIG. 3 is a schematic process diagram illustrating one embodiment of a heart rate estimation process 101. The process 101 may be performed by the electronic device 105. The process 101 is described in more detail in FIG. 5. In the depicted embodiment, an OOI module 320, an ROI module 325, a super pixel calculator 330, a pre-processor 335, a modeler 340, an optimizer 345, and a heart rate detector 350 perform the process 101. The OOI module 320, ROI module 325, super pixel calculator 330, pre-processor 335, modeler 340, optimizer 345, and heart rate detector 350 may be embodied in semiconductor hardware and/or code executed by a processor.

The OOI module 320 may receive the video data 120 from a camera of the electronic device 105 and detect an OOI 285. The OOI module 320 may track the OOI 285 using the camera and generate OOI data 440 that describes the OOI 285. The ROI module 325 may receive the OOI data 440 and identify an ROI 250 within the OOI 285. The ROI module 325 may generate ROI data 425 that describes the ROI 250.

The super pixel calculator 330 may receive the ROI data 425 and generate super pixels 240 in a super-pixel time series 195. The preprocessor 335 may preprocess the super-pixel time series 195 to remove interfering signals from the super-pixel time series 195 and generate a preprocessed super-pixel time series 290.

The modeler 340 may generate the super pixel model 270 from the super-pixel time series 195 and/or the preprocessed super-pixel time series 290. The optimizer 345 may calculate a heartbeat signal 255 from the super-pixel model 270. In one embodiment, the optimizer 345 calculates a heart beat signal 465 from the super-pixel model 270 and the preprocessed super-pixel time series 290. The heart rate detector 350 may calculate heart characteristics such as a heart rate 480, an inter-beat interval 475, and/or a heart rate variability 490 from the heartbeat signal 465.

Figure 4:
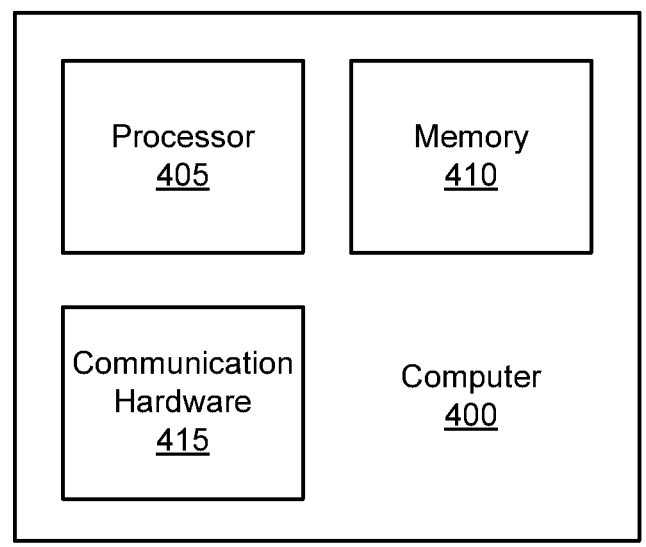
FIG. 4 is a schematic block diagram illustrating one embodiment of a computer.

FIG. 4 is a schematic block diagram illustrating one embodiment of a computer 400. The computer 400 may be embodied in the electronic device 105. The computer 400 includes a processor 405, a memory 410, and communication hardware 415. The memory 410 may be a computer readable storage medium such as a semiconductor storage device, a hard disk drive, a holographic storage device, a micromechanical storage device, or combinations thereof. The memory 410 may store code. The processor 405 may execute the code. The communication hardware 415 may communicate with other devices.

Figure 5:
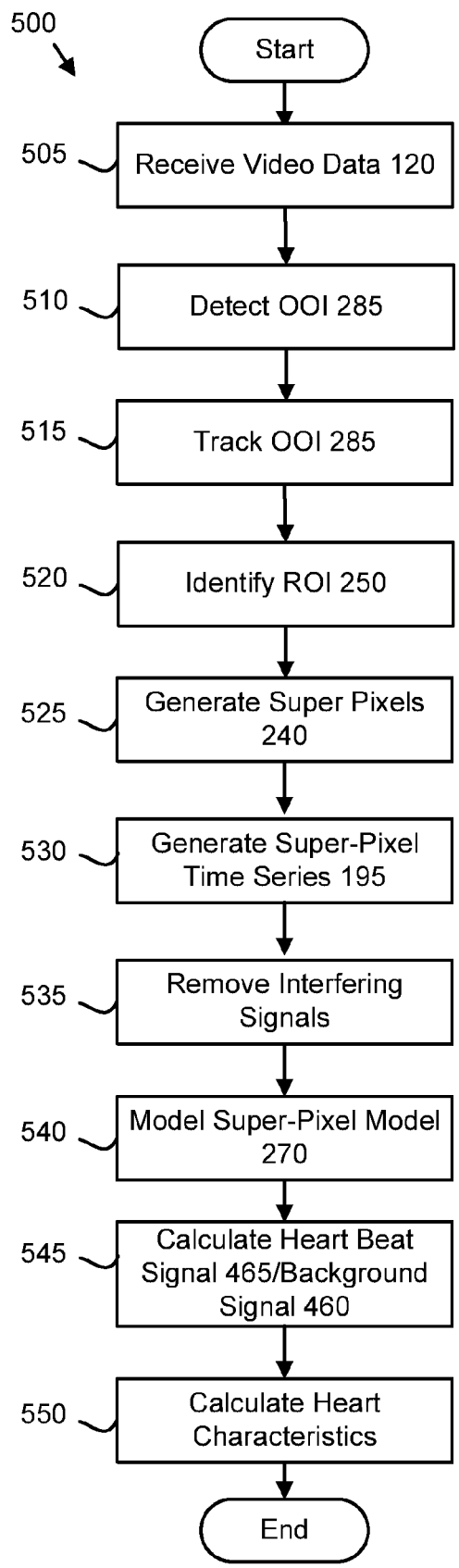
FIG. 5 is a schematic flowchart diagram illustrating one embodiment of a heart rate estimation method.

FIG. 5 is a schematic flowchart diagram illustrating one embodiment of a heart rate estimation method 500. The method 500 may remotely estimate a heart rate. The method 500 may be performed by the processor 405 and/or the OOI module 320, ROI module 325, super pixel calculator 330, pre-processor 335, modeler 340, optimizer 345, and heart rate detector 350 in the electronic device 105.

The method 500 starts, and in one embodiment, the electronic device 105 receives 505 the video data 120 from the camera of the electronic device. In one embodiment, the video data 120 is received as one or more time series 125 of pixels 225.

The electronic device 105 further detects 510 the OOI 285 in each image of the video data 120. The image may comprise pixels 225 for a time series 125. The OOI 285 may be a subject and/or a body part of the subject 115 such as a head, a neck, and arm, leg, or the like. In one embodiment, the OOI 285 is detected using cascaded object detection on RGB pixels of the video data 120.

The electronic device 105 may further track 515 the OOI 285 in each image of the video data 120. In one embodiment, the OOI 285 is tracked using infrared band information from an infrared camera and/or a multi-spectral camera. The electronic device 105 may generate OOI data 440 that represents the OOI 285

The electronic device 105 may identify 520 one or more ROI 250 within the OOI 285. The ROI 250 may be a region of a body part such as a forehead, a wrist, and the like. In one embodiment, the ROI 250 is identified using image segmentation. The electronic device 105 may generate ROI data 425 that represents the ROI 250.

The electronic device 105 may generate 525 super pixels 240 in each ROI 250 from the video data 120 and the ROI data 425. In one embodiment, each super pixel 240 includes a specified number of pixels 225. Alternatively, each super pixel 240 may be formed of adjacent pixels 225 with measured pixel values 265 within a value range.

The electronic device 105 may further generate 530 a super-pixel time series 195 for a plurality of super pixels 240 in each image of the video data 120. In one embodiment, one or more sequential super pixels 240 are concatenated to form the super-pixel time series 195. Alternatively, one or more non-sequential super pixels 240 are selected and concatenated to form the super-pixel time series 195.

The electronic device 105 may remove 535 interfering signals from the super-pixel time series 195. The removal of the interfering signals may be preprocessing. In one embodiment, the interfering signals are removed 535 using de-trending. The de-trending may be performed by modeling the background signal 460 as a Gaussian process. Alternatively, the de-trending may be performed by decorrelating the super-pixel time series 195 with auxiliary signals derived from the position of a facebox that bounds a face of a subject 115 and from other regions in the video data 120. In one embodiment, removing 535 the interfering signals from the super-pixel time series 195 comprises band pass filtering to remove signals outside a frequency band of normal heart rate. For example, signals with a frequency below 40 beats per minute (bpm) and above 170 bpm may be filtered from the super-pixel time series 195.

The electronic device 105 may model 540 the super-pixel time series 195 as the super-pixel model 270. In one embodiment, the super-pixel time series 195 is modeled in the form of Equation 1.

The electronic device 105 may calculate 545 the heartbeat signal 465 using the super-pixel model 270. In one embodiment, the heartbeat signal 465 and the background signal 460 are calculated 545 by optimizing Equation 2 subject to Equations 3 and 4. In one embodiment, the sum on i is over the plurality of super pixels 240, and the sum on t is over the plurality of super pixels 240 in the time series 125, $\lambda_1$ and $\lambda_2$ are user parameters, H is an $(M+1) \times (2L+1)$ Toeplitz matrix having $(i,j)^{th}$ element $h(2L+i-j)$ for $i=1, 2, \ldots, M+1$ and $j=1, 2, \ldots, 2L+1$, h is an $(M+1) \times 1$ vector having $i^{th}$ element $h(L+T+i-1)$ for $i=1, 2, \ldots, M+1$, and $\|\bullet\|_*$ is a nuclear norm.

$$\min_{u_i(t),\, h(t)} \sum_i \sum_t |y_i(t) - u_i(t) - h(t)|^2 +$$
$$\lambda_1 \|[H \mid h]\|_* + \lambda_2 \sum_i \sum_t |u_i(t+1) - u_i(t)|^2 \quad \text{Equation 2}$$

$$[H]_{(i,j)} = h(2L + i - j) \quad \text{Equation 3}$$

$$[h]_i = h(L + T + i - 1) \quad \text{Equation 4}$$

Alternatively, the heartbeat signal 465 and the background signal 460 are calculated 545 by optimizing Equation 5, where D is given by Equation 6 and P is given by Equation 7, and $\alpha$ and $\beta$ are user selectable constants that generate the smoothness of the background signal 460 and/or the predictability of the heart beat signal 465. The vector u contains samples of the background signal and the vector h contains samples of the heart beat signal. The prediction coefficients $p_L, \ldots, p_{-L}$ are interpolation coefficients derived from a hypothesized period of the heart beat signal 465 and the placement of the $-1$ in the P matrix is also dependent on the hypothesized period of the heart beat signal 465. This optimization may be repeated for a series of different heart beat periods and a first heart beat period giving the smallest objective value may be chosen as the period of the heart beat signal 465.

$$\min_{u,h} \left\| \begin{bmatrix} y \\ 0 \\ 0 \end{bmatrix} - \begin{bmatrix} I & I \\ \alpha D & 0 \\ 0 & \beta P \end{bmatrix} \begin{bmatrix} u \\ h \end{bmatrix} \right\| \quad \text{Equation 5}$$

$$D = \begin{bmatrix} -1 & 1 & & \\ & -1 & 1 & \\ & & \ddots & \ddots \\ & & & -1 & 1 \end{bmatrix} \quad \text{Equation 6}$$

$$P = \begin{bmatrix} p_L & \cdots & p_{-L} & 0 & 0 & -1 & 0 & 0 & 0 \\ & \ddots & & \ddots & & & \ddots & & \\ & & \ddots & & \ddots & & & \ddots & \\ 0 & 0 & 0 & p_L & \cdots & p_{-L} & 0 & 0 & -1 \end{bmatrix} \quad \text{Equation 7}$$

In one embodiment, the electronic device 105 calculates 550 the heartbeat characteristics from the heartbeat signal 465 and the method 500 ends. The heartbeat characteristics may include the heart rate 480, the inter-beat interval 475, and/or the heart rate variability 490. The electronic device 105 may calculate 550 the heart rate 480 using one or more of a machine learning analysis of the heart beat signal 465, a peak of a Fourier transform of the heart beat signal 465, a power spectral density of the heart beat signal 465, a zero crossing rate of the heart beat signal 465, or a sliding correlation analysis of the heart beat signal 465.

The embodiments detect the OOI 285 from video data, track the OOI 285, and identify the ROI 250 within the OOI 285. The embodiments further generate super pixels 240 from pixels 225 within the ROI 250. In addition, the embodiments generate a super-pixel time series 195 and modeled the super-pixel time series 195 as a super-pixel model 270. The super pixel model 270 is used to calculate the heartbeat signal 265 and other heart characteristics. As a result, the embodiments are able to remotely estimate a heart rate 480 of one or more subjects 115. The embodiments allow, for example, the heart rates 480 of animals to be remotely estimated, the heart rates 480 of human subjects 115 to be estimated in situations where the subjects 115 are active, and for the rapid determination of the heart rate 480. As a result, the embodiments provide a practical and effective way for remote estimation of heart rates 480.

The embodiments may be practiced in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method comprising:
   detecting, by use of a processor, an object of interest (OOI) in each image of a video data;
   tracking the OOI in each image of the video data;
   identifying a region of interest (ROI) within the OOI;
   generating a plurality of super pixels from a plurality of pixels in each ROI;
   generating a super-pixel time series from the plurality of super pixels in each image;
   removing interfering signals from the super-pixel time series;
   modeling the super-pixel time series as a super-pixel model;

calculating a heart beat signal from the super-pixel model, wherein an ith super pixel for a time t is modeled as $y_i(t)=u_i(t)+h_i(t)+n_i(t)$, where $y_i(t)$ is a measured pixel value, $u_i(t)$ is a background signal representing contributions to the measured pixel value due to movement and lighting variations, $h_i(t)$ is the heart beat signal, and $n_i(t)$ is a sensor noise signal representing contributions to the measured pixel value due to sensor noise; and calculating heart characteristics from the heart beat signal, the heart characteristics comprising one or more of a heart rate, an inter-beat interval, and a heart rate variability.

2. The method of claim 1, wherein the sensor noise signal $n_i(t)$ is assumed to be independent, identically distributed Gaussian noise.

3. The method of claim 1, wherein the background signal $u_i(t)$ is assumed to be smooth.

4. The method of claim 3, wherein the background signal $u_i(t)$ is modeled as a first order Markov random process.

5. The method of claim 1, wherein the heart beat is assumed to be the same in each super pixel, wherein $h_i(t)=h(t)$ for all i.

6. The method of claim 1, wherein the heart beat signal and a background signal are further calculated by optimizing $$\min_{u_i(t),\, h(t)} \sum_i \sum_t |y_i(t)-u_i(t)-h(t)|^2 + \lambda_1 \|[H\,|\,h]\|_* + \lambda_2 \sum_i \sum_t |u_i(t+1)-u_i(t)|^2$$

subject to $[H]_{(i,j)}=h(2L+i-j)$ and $[h]_i=h(L+T+i-1)$, where the sum on i is over the plurality of super pixels, and the sum on t is over the plurality of super pixels in the super pixel time series, $\lambda_1$ and $\lambda_2$ are user parameters, H is an $(M+1)\times(2L+1)$ Toeplitz matrix having $(i,j)^{th}$ element $h(2L+i-j)$ for $i=1, 2, \ldots, M+1$ and $j=1, 2, \ldots, 2L+1$, h is an $(M+1)\times 1$ vector having $i^{th}$ element $h(L+T+i-1)$ for $i=1, 2, \ldots, M+1$, and $\|\cdot\|_*$ is a nuclear norm.

7. The method of claim 1, wherein the heart beat signal and a background signal are further calculated by optimizing $$\min_{u,h} \left\| \begin{bmatrix} y \\ 0 \\ 0 \end{bmatrix} - \begin{bmatrix} I & I \\ \alpha D & 0 \\ 0 & \beta P \end{bmatrix} \begin{bmatrix} u \\ h \end{bmatrix} \right\|$$

where $$D = \begin{bmatrix} -1 & 1 & & \\ & -1 & 1 & \\ & & \ddots & \ddots \\ & & & -1 & 1 \end{bmatrix}$$

$$P = \begin{bmatrix} p_L & \cdots & p_{-L} & 0 & 0 & -1 & 0 & 0 & 0 \\ & \ddots & & \ddots & & & \ddots & & \\ & & \ddots & & \ddots & & & \ddots & \\ 0 & 0 & 0 & p_L & \cdots & p_{-L} & 0 & 0 & -1 \end{bmatrix}$$

and $\alpha$ and $\beta$ are user selectable constants selected to generate a smoothness of the background signal and a predictability of the heart beat signal, the vector u contains samples of the background signal and the vector h contains samples of the heart beat signal, the prediction coefficients $p_L, \ldots, p_{-L}$ are interpolation coefficients derived from a hypothesized period of the heart beat signal and a placement of the −1 in the P matrix is also dependent on a hypothesized period of the heart beat signal, and wherein an optimization is repeated for a series of different heart beat periods and a first heart beat period giving the smallest objective value is chosen as a period of the heart beat signal.

8. The method of claim 1, wherein the OOI is detected using cascaded object detection on red/green/blue (RGB) pixels of the video data and the OOI is tracked with sub-pixel resolution using spatial correlation-based methods.

9. The method of claim 1, wherein the OOI is detected and tracked using infrared band information.

10. The method of claim 1, wherein the video data is captured by one or more of a plurality of cameras, 3-color channel camera, a multispectral n-channel camera, an infrared camera, a depth camera, a 1 pixel sensor, and a servo controlled camera.

11. The method of claim 1, wherein each super pixel comprises one or more measured pixel values representing an average value of pixels in the ROI.

12. The method of claim 1, wherein the heart rate is calculated using one of a machine learning analysis of the heart beat signal, a peak of a Fourier transform of the heart beat signal, a power spectral density of the heart beat signal, a zero crossing rate of the heart beat signal, and a sliding correlation analysis of the heart beat signal.

13. The method of claim 1, wherein removing the interfering signals from the super-pixel time series comprises de-trending by modeling a background signal as a Gaussian process.

14. The method of claim 1, wherein removing the interfering signals from the super-pixel time series comprises de-trending by decorrelating the super-pixel time series with auxiliary signals derived from a position of a facebox and from other regions in the video data.

15. The method of claim 1, wherein removing the interfering signals comprises band pass filtering to remove signals outside a frequency band of a normal heart rate.

16. An apparatus comprising:
a camera;
a processor;
a memory storing code executable by the processor to perform:
detecting an object of interest (OOI) in each image of a video data captured by the camera;
tracking the OOI in each image of the video data;
identifying a region of interest (ROI) within the OOI;
generating a plurality of super pixels from a plurality of pixels in each ROI;
generating a super-pixel time series from the plurality of super pixels in each image;
removing interfering signals from the super-pixel time series;
modeling the super-pixel time series as a super-pixel model;
calculating a heart beat signal from the super-pixel model, wherein an ith super pixel for a time t is modeled as $y_i(t)=u_i(t)+h_i(t)+n_i(t)$, where $y_i(t)$ is a measured pixel value, $u_i(t)$ is a background signal representing contributions to the measured pixel value due to movement and lighting variations, $h_i(t)$ is the heart beat signal, and $n_i(t)$ is a sensor noise signal representing contributions to the measured pixel value due to sensor noise; and calculating heart characteristics from the heart beat signal, the heart characteristics comprising one or more of a heart rate, an inter-beat interval, and a heart rate variability.

17. The apparatus of claim 16, wherein the heart beat signal and a background signal are further calculated by optimizing $$\min_{u_i(t),\, h(t)} \sum_i \sum_t |y_i(t) - u_i(t) - h(t)|^2 + \lambda_1 \|[H\,|\,h]\|_* + \lambda_2 \sum_i \sum_t |u_i(t+1) - u_i(t)|^2$$

subject to $[H]_{(i,j)} = h(2L+i-j)$ and $[h]_i = h(L+T+i-1)$, where the sum on i is over the plurality of super pixels, and the sum on t is over the plurality of super pixels in the super pixel time series, $\lambda_1$ and $\lambda_2$ are user parameters, H is an $(M+1) \times (2L+1)$ Toeplitz matrix having $(i,j)^{th}$ element $h(2L+i-j)$ for $i=1, 2, \ldots, M+1$ and $j=1, 2, \ldots, 2L+1$, h is an $(M+1) \times 1$ vector having $i^{th}$ element $h(L+T+i-1)$ for $i=1, 2, \ldots, M+1$, and $\|\bullet\|_*$ is a nuclear norm.

18. The apparatus of claim 16, wherein the heart beat signal and a background signal are further calculated by optimizing $$\min_{u,h} \left\| \begin{bmatrix} y \\ 0 \\ 0 \end{bmatrix} - \begin{bmatrix} I & I \\ \alpha D & 0 \\ 0 & \beta P \end{bmatrix} \begin{bmatrix} u \\ h \end{bmatrix} \right\|$$

where $$D = \begin{bmatrix} -1 & 1 & & \\ & -1 & 1 & \\ & & \ddots & \ddots \\ & & & -1 & 1 \end{bmatrix}$$

$$P = \begin{bmatrix} p_L & \cdots & p_{-L} & 0 & 0 & -1 & 0 & 0 & 0 \\ & \ddots & & \ddots & & & \ddots & & \\ & & \ddots & & \ddots & & & \ddots & \\ 0 & 0 & 0 & p_L & \cdots & p_{-L} & 0 & 0 & -1 \end{bmatrix}$$

and $\alpha$ and $\beta$ are user selectable constants selected to generate a smoothness of the background signal and a predictability of the heart beat signal, the vector u contains samples of the background signal and the vector h contains samples of the heart beat signal, the prediction coefficients $p_L, \ldots, p_{-L}$ are interpolation coefficients derived from a hypothesized period of the heart beat signal and a placement of the $-1$ in the P matrix is also dependent on a hypothesized period of the heart beat signal, and wherein an optimization is repeated for a series of different heart beat periods and a first heart beat period giving the smallest objective value is chosen as a period of the heart beat signal.

19. A program product comprising a non-transitory computer readable storage medium storing code executable by a processor to perform:
  detecting an object of interest (OOI) in each image of a video data captured by the camera;
  tracking the OOI in each image of the video data;
  identifying a region of interest (ROI) within the OOI;
  generating a plurality of super pixels from a plurality of pixels in each ROI;
  generating a super-pixel time series from the plurality of super pixels in each image;
  removing interfering signals from the super-pixel time series;
  modeling the super-pixel time series as a super-pixel model;
  calculating a heart beat signal from the super-pixel model, wherein an ith super pixel for a time t is modeled as $y_i(t) = u_i(t) + h_i(t) + n_i(t)$, where $y_i(t)$ is a measured pixel value, $u_i(t)$ is a background signal representing contributions to the measured pixel value due to movement and lighting variations, $h_i(t)$ is the heart beat signal, and $n_i(t)$ is a sensor noise signal representing contributions to the measured pixel value due to sensor noise; and
  calculating heart characteristics from the heart beat signal, the heart characteristics comprising one or more of a heart rate, an inter-beat interval, and a heart rate variability.

20. The program product of claim 19, wherein the heart beat signal and a background signal are further calculated by optimizing $$\min_{u_i(t),\, h(t)} \sum_i \sum_t |y_i(t) - u_i(t) - h(t)|^2 + \lambda_1 \|[H\,|\,h]\|_* + \lambda_2 \sum_i \sum_t |u_i(t+1) - u_i(t)|^2$$

subject to $[H]_{(i,j)} = h(2L+i-j)$ and $[h]_i = h(L+T+i-1)$, where the sum on i is over the plurality of super pixels, and the sum on t is over the plurality of super pixels in the super pixel time series, $\lambda_1$ and $\lambda_2$ are user parameters, H is an $(M+1) \times (2L+1)$ Toeplitz matrix having $(i,j)^{th}$ element $h(2L+i-j)$ for $i=1, 2, \ldots, M+1$ and $j=1, 2, \ldots, 2L+1$, h is an $(M+1) \times 1$ vector having $i^{th}$ element $h(L+T+i-1)$ for $i=1, 2, \ldots, M+1$, and $\|\bullet\|_*$ is a nuclear norm.

* * * * *